United States Patent [19]

Moasser

[11] 4,245,358
[45] Jan. 20, 1981

[54] NONTRAUMATIC PROSTHETIC VALVE WITH MAGNETIC CLOSURE

[76] Inventor: Manoutcher Moasser, Rte. 301 & Central Ave., Waldorf, Md. 20601

[21] Appl. No.: 6,027

[22] Filed: Jan. 24, 1979

[51] Int. Cl.³ .............................................. A61F 1/22
[52] U.S. Cl. ........................................ 3/1.5; 137/847; 137/533.11; 251/65
[58] Field of Search ........ 3/1.5; 128/350 V, DIG. 25; 251/65; 137/844, 846, 847

[56] References Cited

U.S. PATENT DOCUMENTS

| | | | |
|---|---|---|---|
| 3,409,038 | 11/1968 | Blackford | 251/65 X |
| 3,736,598 | 6/1973 | Bellhouse et al. | 3/1.5 |
| 3,898,701 | 8/1975 | La Russa | 3/1.5 |
| 3,959,827 | 6/1976 | Kaster | 3/1.5 |

OTHER PUBLICATIONS

"The Direct Approach for the Correction of Aortic Insufficiency" by C. A. Hufnagel et al., J.A.M.A., vol. 178, No. 3, Oct. 21, 1961, pp. 275-279.
"Comparative Study of Some Prosthetic Valves for Aortic and Mitral Replacement" by C. A. Hufnagel et al., Surgery, vol. 57, No. 1, Jan. 1965, pp. 205-210.

Primary Examiner—Ronald L. Frinks
Attorney, Agent, or Firm—Sixbey, Friedman & Leedom

[57] ABSTRACT

An improved valve prosthesis for causing nontraumatic unidirectional flow of a pulsatory fluid, such as blood, through a conduit, such as a blood vessel. The valve includes two flaps, made of a suitable flexible material, attached by the proximal ends to opposite sides of a covered annular mounting structure. A pair of magnetic members are connected to the distal ends of the flaps thereby to exert sufficient attractive force to hold the flaps together in a closed position to prevent fluid flow through the valve. The magnetically-closed flaps are forced to an open position by the pressure of the fluid flowing through the conduit. A decrease in fluid pressure in combination with the attractive force exerted by the magnetic members permits the smooth, nontraumatic closure of the valve flaps.

10 Claims, 12 Drawing Figures

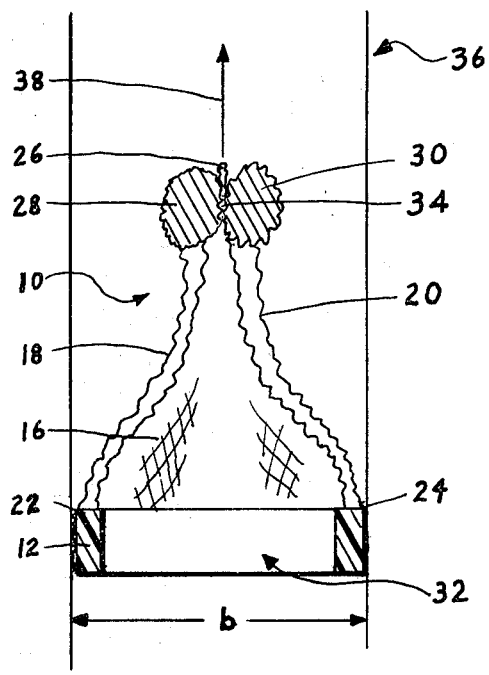
FIG. 4
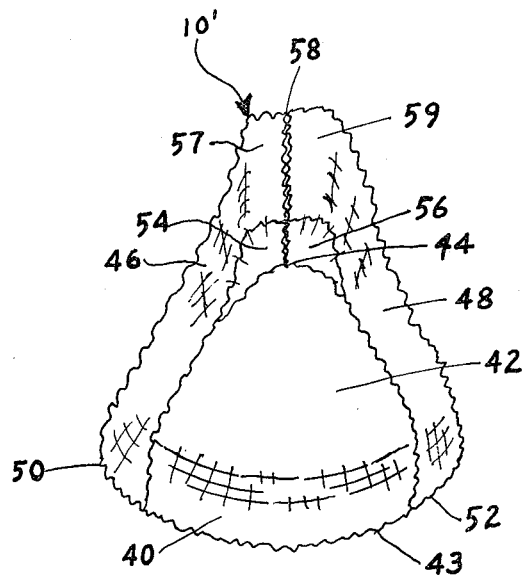
FIG. 5
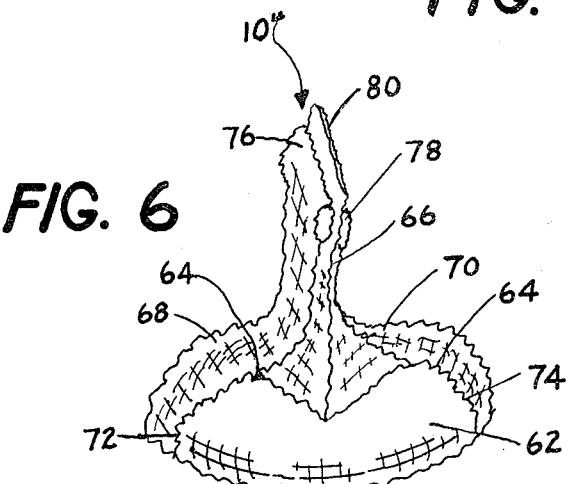
FIG. 6
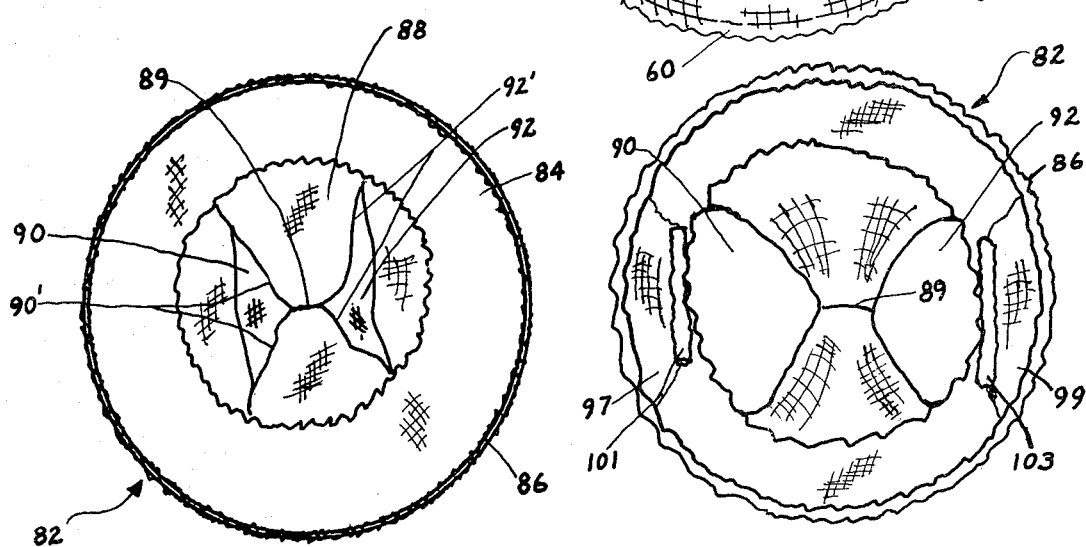
FIG. 7A
FIG. 7B

NONTRAUMATIC PROSTHETIC VALVE WITH MAGNETIC CLOSURE

TECHNICAL FIELD

The present invention relates generally to an improved valve for controlling the unidirectional flow of a pulsatory fluid and, more specifically, to a valve prosthesis which provides for the nontraumatic control of body fluid flow, such as blood flow through the heart of a human or animal, by means of two flexible flaps attached at the proximal ends to opposite sides of a mounting ring, which flaps include at their distal ends magnetic members which exert an attractive force of sufficient magnitude to hold the flaps together in a closed position when the fluid flow has subsided but not of such a magnitude to prevent the opening of the flaps in response to the pressure normally exerted by the fluid.

BACKGROUND ART

Artificial valves, both those used as prosthetic devices within the human and animal body and those used to control the flow of body fluids externally, have long been known to the medical profession. The prior art valves used primarily as prosthetic devices have taken many forms in an attempt to replicate the function of the natural valves which they replace. None of these prior art valves, however, has fully achieved the replication of a naturally occurring valve. Lack of success has resulted in part from problems with long term durability of the valve itself and from differences between actual and measured fluid flow area provided by the valve which has resulted in undesirable pressure gradients across the valve. In addition, prior art valves increase, rather than reduce or eliminate, the turbulence created by the passage of the fluid through and the subsequent closure of the valve. Such turbulence results in greatly increased hemolysis when the fluid flowing through the valve is blood.

Prior art prosthetic valves conform, for the most part, to three general types. The ball and cage valve, such as that described in U.S. Pat. No. 3,416,159, is illustrative of one type. The valve ball, usually constructed of silicone rubber, is susceptible to variance in shape, fractures of the ball surface and subsequent lipid infiltration into the ball. Additional complications which often accompany this type of valve include fibrin clot formation, which further interfers with the movement of the ball in the cage, and thrombosis. Because of these complications, the patient with this type of prosthesis must undergo continuous anticoagulant therapy. Moreover, singe the ball portion of the valve must be located in the center of the cage to allow proper functioning of the valve, fluid flow through this type of valve cannot be central, as in a natural valve, but is directed through the valve around the periphery of the ball. The turbulence resulting from this, coupled with the turbulence created by closure of the valve, causes a higher level of hemolysis and blood cell damage than is desirable. The presence of the ball in the center of the blood vessel also imparts an unnatural radial component to the flow of blood within the vessel producing injury to the walls of the vessel against which the radial component is directed. Ball and cage valves are large in size and therefore can present difficulties in insertion. They have also been disturbing to some persons into whom they have been inserted because of the audible sound detectable upon closing. Attempts to correct the deficiencies of the ball and cage type valve by replacing the ball with a disc shaped element have generally been unsuccessful.

A second type of prior art valve, generally referred to as a tissue valve, is composed of a stent or mounting ring to which human or animal tissue has been attached in a form which approximates the flaps in a natural valve. However, the long-term durability of these valves is still a matter of concern. Construction of the tissue valve from cadaver material such as fascia lata results in a valve with low durability because of rapid tissue degradation and stiffening and has led to tissue dysfunction and subsequent valve immobility. While another variation of the tissue valve, the glutaraldehyde-fixed porcine xenograft, illustrated by U.S. Pat. No. 4,084,268 to Ionescu et al, has not been as prone to these problems, degradation and calcification of the tissue matrix resulting in valve dysfunction have been reported. Moreover, Johnson et al. in The Journal of Thoracic and Cardiovascular Surgery 75:599–605, 1978, concluded that functional stenosis or narrowing of the blood vessel was commonly encountered when the porcine xenograft was used to replace the aortic valve. Moreover, since these valves rely entirely on back pressure for closure, closure is accompanied by increased trauma to the blood cells and the greater likelihood of valve incompetence than encountered with a natural valve.

U.S. Pat. Nos. 3,197,788 to Segger and 3,736,598 to Bellhouse et al described prosthetic cardiac valves that are similar to tissue valves in their structure, but are made of flexible synthetic materials. Both valves disclosed in U.S. Pat. Nos. 3,197,788 and 3,736,598 imitate the natural valve by providing three cusps or flaps, which comprise the valve members, attached to a supporting ring. The valves open in response to the pressure exerted on them during systole and close in response to the back pressure exerted on the flaps during diastole. However, this closure is quick and somewhat traumatic and enhances the likelihood of increased turbulence and subsequent damage to the blood cells.

A third category of prosthetic valve is the disc type, which is generally formed of an annular base to which a disc-shaped valving member is secured, either by means of a magnetic hinge, as in U.S. Pat. No. 3,370,305 to Goott, by means of an eccentrically-placed stem, as in the Modified University of Capetown Prosthesis described by Ellis et al, in The Annals of Thoracic Surgery 23:26–31, 1977, or by means of a rod along which the disc can be displaced, as in U.S. Pat. No. 3,959,827 to Kaster. Although fluid flow through this type of valve is more centralized than through the ball and cage valve, increased hemolysis results from turbulence created by fluid flow through the valve. In addition, injury to the walls of the blood vessel beyond the valve results from the radial components imparted to the blood flow caused by the presence of the valve disc in the blood stream. Moreover, use of this valve necessitates the institution of long-term anticoagulant therapy because of the high level of thrombogenesis which accompanies the use of the valve. As reported in The Annals of Thoracic Surgery 23:26–31, 1977, Ellis et al discontinued use of one type of tilting disc prosthesis, in part because of the excessive incidence of thromboembolism and in part because the effective valve orifice area after the valve had been in place was usually considerably less than the measured orifice area before insertion.

In U.S. Pat. No. 3,959,827, Kaster discloses one embodiment of a disc type valve in which the closing of the valve is assisted by means of a permanent magnet located in the disc valving member. Although this permits a smoother closing than is possible without the magnet, the disc valve disclosed in U.S. Pat. No. 3,959,827 still suffers from the other drawbacks generally common to disc type valves. Forman et al reported in The Journal of Thoracic and Cardiovascular Surgery 75:595–598, 1978, that they no longer recommended the use of a tilting disc valve similar to the one disclosed in U.S. Pat. No. 3,959,827, in large part because of a high incidence of embolism and valvular thrombosis, but also because the effective orifice area of the valve was less than the actual orifice area. In addition, they found that this type of valve demonstrated no clear hemodynamic advantage over other available prostheses.

Valves used for medical purposes in which valve closing is magnetically assisted are disclosed in U.S. Pat. Nos. 3,233,610 to Wade, 3,495,620 to Raimondi et al and 3,926,175 to Allen et al. The valves described in U.S. Pat. Nos. 3,233,610 and 3,495,620 provide fluid flow orifices through only a portion of the valve diameter, thus resulting in a slow fluid flow area in relation to valve diameter. The magnetically actuated valve disclosed in U.S. Pat. No. 3,926,175 is incapable of operating in response to fluid pressure within a body vessel and is thus unable to operate automatically to cause unidirectional flow of a pulsatory fluid.

DISCLOSURE OF THE INVENTION

It is a general object of this invention to overcome the deficiencies of the prior art relating to artificial and prosthetic valves as discussed above.

It is a more specific object of this invention to provide an improved valve for producing unidirectional flow of a pulsatory fluid through a conduit and, more specifically, to provide an improved prosthetic valve for the nontraumatic control of the flow of body fluids through human and animal vessels.

It is an object of the present invention to provide a prosthetic valve with good hemodynamic characteristics, a valve that provides less obstruction of the valve orifice area than prior art valves when fully open and a valve that is competent when shut. More particularly, the valve of the present invention provides a valve structure comprised of an annular mounting structure to which is attached at their proximal ends two opposed, spaced flexible flaps, which flaps include at their distal ends magnetic members with sufficient attractive force to hold the flaps tightly together in the closed position, but may be opened by fluid pressure so that substantially the entire vessel diameter is available for fluid flow.

It is another object of the present invention to provide a prosthetic valve characterized by a greater satisfactory operating life, compared to previously known valve designs, during which the valve will not degenerate or wear out and will be free from variance. The valve of the present invention is constructed of durable synthetic materials which, in combination with the novel structure, fulfill the stated objectives.

It is a further object of the present invention to provide a prosthetic valve that does not significantly alter blood components and causes only minimal hemolysis. The novel structure of the present invention provides flexible flaps which include magnetic members at their distal ends, which flaps are closed gently during diastole by a combination of the pressure gradient and the attractive force between the magnets. Such closure is rapid, but smooth, and eliminates the turbulence and subsequent hemolysis characteristics of prior art valves.

It is another object of the present invention to provide a prosthetic valve that is antithrombogenic, thus eliminating the need for the long-term administration of anticoagulants an their attendant complications. The novel structure of the present invention includes no surfaces upon which fibrin clots are likely to form and, in addition, may be constructed of a synthetic fabric widely used for arterial grafts, the use of which specifically contra-indicates anticoagulant therapy.

Other objects of the present invention include providing a prosthetic valve which can be inserted into a body conduit without undue difficulty and which does not disturb the person or animal into which it is inserted, such as by making an audible noise upon closing. The annular mounting structure can be made in sizes to conform to the internal diameters of the vessels into which it is to be inserted. Additionally, the flexible synthetic material of the flaps is used to cover the mounting ring, thus providing a means of easily suturing the valve to the vessel. The soft, nontraumatic closing of the flaps of the present invention assisted by the attractive forces exerted by the magnets in the distal ends of the flaps is quiet and avoids disturbance to the person or animal in which the valve is implanted.

Additional objects, advantages and features of the invention will be more readily apparent from the following detailed description of a preferred embodiment of the invention when taken together with the accompanying drawings.

BRIEF DESCRIPTION OF THE DRAWINGS

FIG. 4 is a cross-sectional view of the valve of FIG. 1 showing it located within a conduit in the closed position;

FIG. 5 is a drawing in perspective of a second embodiment of the present invention;

FIG. 6 is a drawing in perspective of a third embodiment of the present invention;

FIG. 7 A and B are elevational views of the valve orifice of a fourth embodiment of the present invention with the valve in a closed and open position, respectively;

DESCRIPTION OF THE PREFERRED EMBODIMENT

Figure 1:
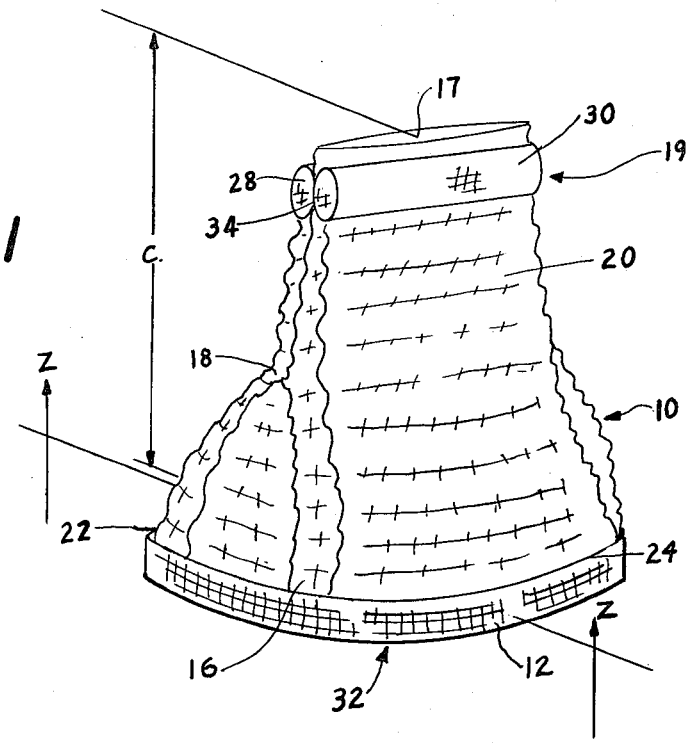
FIG. 1 is a drawing in perspective of one embodiment of the valve of the present invention in a closed position.

Referring to the drawings, FIGS. 1 through 4 depict different views of the same embodiment of the present invention. The improved valve of the present invention, generally referred to as 10, includes an annular mounting structure or mounting ring 12, which may be made of either a rigid or semi-flexible material such as plastic.

The outside diameter b of the annular mounting structure 12 will be determined by the diameter of the conduit or body vessel into which the valve of the present invention is to be inserted.

The annular mounting structure 12 is connected with one end of a tube 16 found formed from a flexible, non-resilient biologically non-reactive, fabric. The internal diameter "a" of central tube 16 should be equal to or slightly less than the outside diameter "b" of annular mounting structure 12. The axial length "c" of central tube 16 will depend on the particular application of the valve of the present invention.

Figure 2:
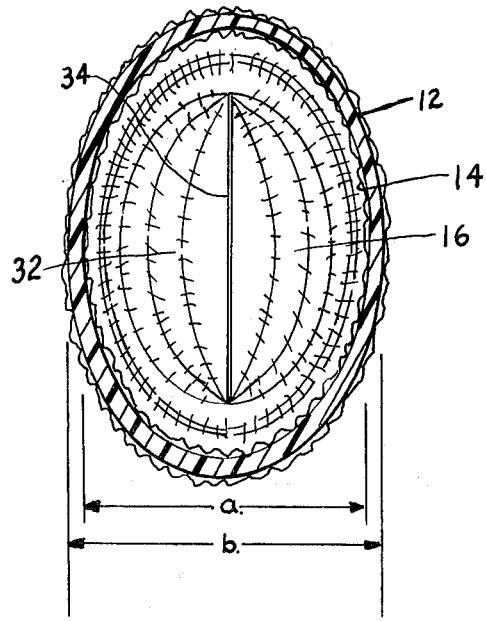
FIG. 2 is a cross-sectional view of the valve taken along lines Z—Z of FIG. 1.
Figure 3:
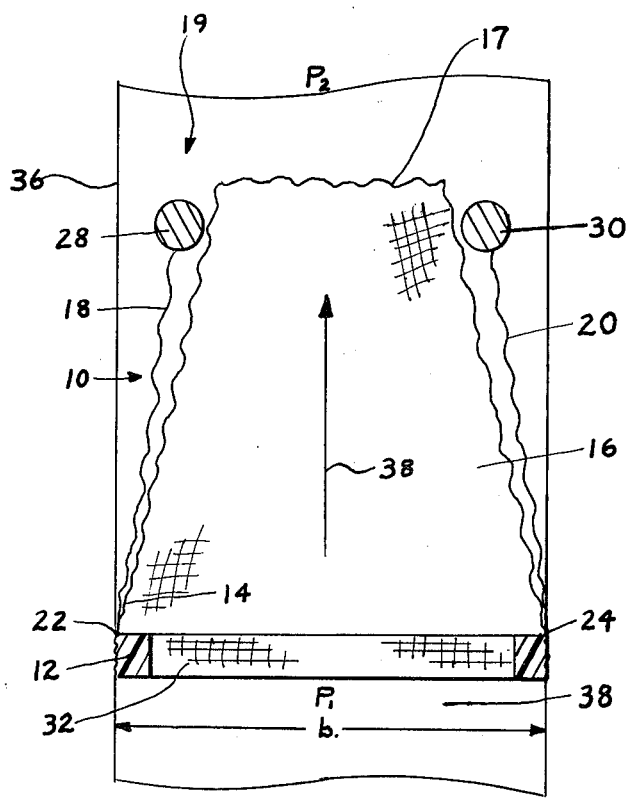
FIG. 3 is a cross-sectional view of the valve of FIG. 1 showing it located within a conduit in the open position.

As can now be appreciated from a consideration of FIGS. 1–3, tube 16 constitutes a tubular element which forms a type of valve outlet means for moving from a first configuration (FIG. 1) in which fluid flow through the valve is cut off to a second configuration (FIG. 3) in which fluid may freely flow through the valve in response to the fluid pressure upstream of the valve increasing above the fluid pressure downstream of the valve. End 14 of tube 16, attached to mounting structure 12, is designed to be placed upstream in a body fluid conduit through which one way flow of body fluid is desired. End 14 of tube 16 is retained in a constantly open condition by mounting structure 12 while the opposite end 17 of flexible tube 16 is left unsupported and is thus held in a closed position (FIGS. 1–2) whenever the fluid pressure $P_1$ upstream of the valve falls below the downstream pressure $P_2$. Upon a reversal of the relative magnitudes of $P_1$ and $P_2$, end 17 of tube 16 is forced open as illustrated in FIG. 3 to allow fluid flow through tube 16.

As illustrated in FIGS. 1 and 3, valve 10 is equipped with closure assistance means 19 for applying a continuous gentle force to opposite sides (or wall segments) of tube end 17 to bias the valve toward the closed position as illustrated in FIGS. 1 and 2. The magnitude of the bias force produced by means 19 is relatively weak and thus the upstream pressure $P_1$ needs to increase only slightly above the downstream pressure $P_2$ in order to overcome the closing force applied by means 19 to open tube end 17.

Closure assistance means 19 includes a pair of flaps 18 and 20 attached at their proximal ends 22 and 24, respectively, to opposite sides of annular mounting structure 12. Flaps 18 and 20 are constructed of the same flexible fabric as tube 16 and terminate short of end 17 of tube 16, as shown in FIG. 1. Alternatively, flaps 18 and 20 may extend beyond end 17 of tube 16 or may be the same length as tube 16. Closure assistance means 19 also includes permanent magnetic members 28 and 30 exerting a mutually attractive force on one another to create the closing force referred to above. To prevent decomposition caused by body fluids, magnetic members 28 and 30 may be encased within the fabric which forms flaps 18 and 20 or may be covered with an inert material and then attached to the distal ends of flaps 18 and 20. Flaps 18 and 20 may be attached only to annular mounting structure 12 at their proximal ends 22 and 24 or additional points of attachment to central tube 16 may be provided anywhere along the length of flaps 18 and 20, for example, at the location of magnetic members 28 and 30.

FIG. 2 illustrates the valve of FIG. 1 in the closed position as it appears in bottom elevational view through the valve orifice, generally shown at 32. The opposed sides of tube end 17 meet along a line 34 as seen in FIG. 2 when the attractive force of magnetic members 28 and 30 brings the opposed sides (or wall segments) together.

In FIGS. 3 and 4, the improved valve 10 of the present invention is shown in cross-section view as it appears when inserted within a fluid conduit 36, such as a blood vessel. FIG. 3 shows valve 10 in an open position as results when upstream pressure $P_1$ has exceeded the downstream pressure $P_2$ sufficiently to overcome the closing force created by magnets 18 and 20. The fluid flow, represented by arrow 38, which follows the opening of tube end 17, maintains the magnetic members 28 and 30 in a spaced apart position until upstream pressure $P_1$ again decreases in magnitude to no more than slightly above or equal to the downstream pressure. At this point, the magnetic attractive force of members 28 and 30 is sufficient to move the opposite sides of tube end 17 into the closed position illustrated in FIG. 4. With this arrangement, it is apparent that the disclosed valve does not rely upon back pressure to cause valve closure as is the case with most types of check valves. Rather, the disclosed closure assistance means 19, in the form of a pair of permanent magnetic members 28 and 30, is able to effect valve closure before the build up of any significant back pressure which would tend to bring the exposed sides of tube end 17 into violent contact.

FIGS. 5, 6 and 7 show three further embodiments of the improved valve of the present invention. In FIG. 5, the valve 10' includes an annular mounting structure 40, similar to ring 12 of FIG. 1, which includes a pair of opposed spaced rigid projections 42 with substantially arcuate terminal ends 44 formed as a integral part of the edge opposite the valve orifice 43. Mounting structure 40 and projections 42 are covered with the same flexible non-resilient synthetic fabric described above with reference to the embodiment of FIGS. 1–4. It is now clear that the embodiment of FIG. 5 includes opposed flaps or wall segments 46 and 48 (formed of the same flexible, non-resilient fabric described above) attached at their proximal ends 50 and 52 to annular mounting structure 40 in the spaces between projections 42. Flaps 46 and 48 and projections 42 cooperate to form a tubular element having an internal flow passage analagous to tube 16. Magnetic members 54 and 56 are enclosed in the fabric of which flaps 46 and 48 are constructed at the distal ends 57 and 59 of flaps 46 and 48, respectively. The valve of FIG. 5 does not utilize a central tube like central tube 16 of FIGS. 1 through 4, but rather relies upon the sealing capability of ends 57 and 59 as well as the sealing capability of flaps 46 and 48 with respective edges of spaced projections 42, as noted above. Projections 42 provide support means for flaps 46 and 48 so that when the valve is in a closed position, as shown in FIG. 5, magnetic members 54 and 56 rest on the terminal ends 44 of projections 42. Magnetic members 54 and 56 must be shaped so that they fit tightly together at 58 and conform securely to the substantially arcuate terminal ends 44 of projections 42 to prevent fluid leakage when the valve is closed.

FIG. 6 illustrates a third valve embodiment 10'' of the present invention. As in the other embodiments, valve 10'' includes an annular mounting structure 60 which includes as an integral part of its upper edge opposite the valve orifice an opposed pair of spaced, rigid projections 62. Each projection 62 includes two substantially arcuate protrusions 64 on the downstream side of the annular structure 60. Annular structure 60 and projections 62 are covered with the flexible fabric hereinbefore described which extends beyond ends 64 to form a central tube 66. Opposed fabric flaps 68 and 70 are attached to annular mounting structure 60 in the spaces between projections 62 at 72 and 74. Flaps 68 and 70 include within their structures at the distal ends magnetic members 76 and 78, which exert sufficient attractive force to compress distal end 80 of central tube 66 into a closed position as shown in FIG. 6. Flaps 68 and 70 are shown terminating short of end 80 of central tube 66. End 80 represents the valve outlet in this embodiment.

Yet a fourth embodiment of the novel structure of the present invention is shown in bottom view in FIG. 7A. The valve of this embodiment, generally depicted at 82, provides an annular mounting structure 84, covered with a ribbed, flexible fabric which has been folded to provide a raised ridge 86 along the outer edge of mounting ring 84. Ridge 86 may be used as a suture collar to facilitate attachment of valve 82 to a body vessel. The flexible fabric covering on mounting ring 84 extends beyond mounting ring 84 to form a central tube 88. In this embodiment, opposite sides of central tube 88 are attached together at 89 to form a bifurcated passage. In FIG. 7A one of the bifurcated passages 90 is closed along line 90' by a portion of tube 88 which extends downstream of point 89. The other bifurcated passage 92 is similarly closed along line 92' along a downward section of tube 88. The portion of tube 88 extending in the downward direction from point 89 is rejoined to form a single passage as illustrated in FIG. 7B wherein a top elevational view of the valve of FIG. 7A is illustrated.

As in the other embodiments hereinbefore described, opposed, spaced fabric flaps, 97 and 99, which include at their distal ends magnetic members 101 and 103, are attached at their proximal ends to annular mounting structure 84.

Figure 8:
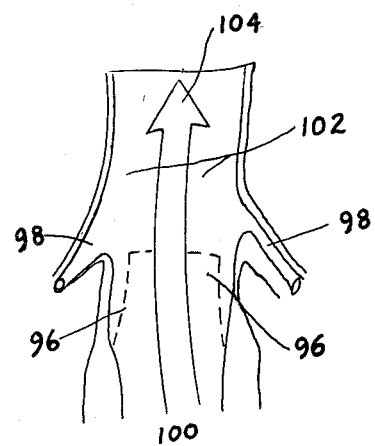
FIG. 8 is a cross-sectional view of a natural heart valve.
Figure 9A:
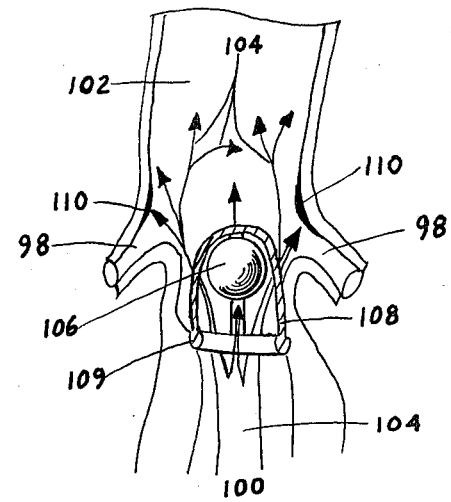
FIGS. 9A–9C are cross-sectional views of various known prosthetic heart valve designs.
Figure 9B:
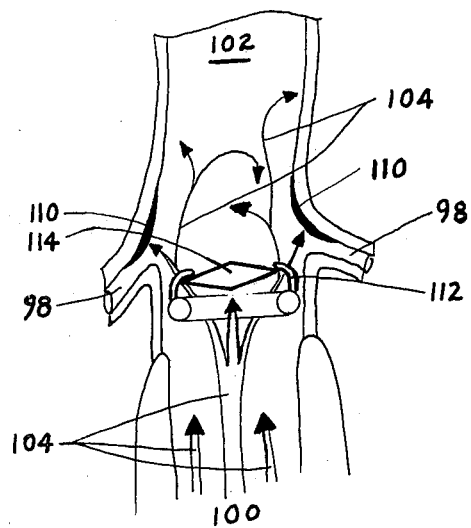
Figure 9C:
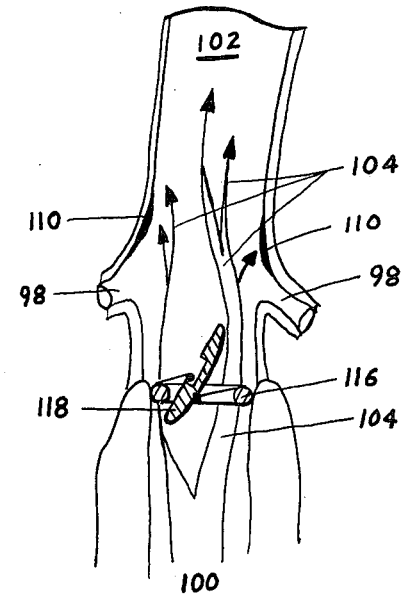

The effects prior art valves have on blood flow in the aorta are depicted in FIGS. 8 and 9A–9C and further demonstrate the advantages of the improved valve of the present invention already discussed. FIG. 8 shows the normal linear flow of the blood at the location of the aortic valve, illustrated schematically at 96, within aorta 102. The coronary arteries are shown at 98 and the left ventricle at 100. Arrow 104 represents the normal centralized flow of blood through the aortic valve. FIG. 9A illustrates the placement of a prosthetic ball and cage valve in the normal aortic valve position. The ball 106 is enclosed within a cage 108. As the blood flow, represented by arrows 104, leaves the left ventricle 100, it passes into the valve, pushing the ball 106 to the top of the cage 109. The flow is prevented from flowing linearly through the valve by the presence of the ball 106. Consequently, the blood flow is diverted around the ball 106 and directed toward points 110 on the walls of the aorta 102, which creates turbulence in the blood and can result in damage to the blood cells. In addition, the pressure exerted by the blood hitting the walls of the aorta at 110 may also cause injury to the vessel wall. Yet another disadvantage of this type of valve is the traumatic effect on the blood cells of both the valve opening and closing. Because ball 106 moves solely in response to blood pressure differentials and flow, significant ball velocity can develop as the ball moves between its open and closed positions. This sudden impact of the ball against cage 108 upon opening and against the valve seat 109 upon closing can have a traumatic effect on the blood cells which are caught between the impacting surfaces. The flexible tube-type valve of the present invention completely avoids these drawbacks of the prior art by providing centralized generally laminar flow through a single or bifurcated valve passage having no pressure induced impacting of valve surfaces either upon opening or closing of the valve. In FIG. 9B, a caged disc-type valve 112 is positioned between the aorta 102 and the left ventricle 100. This type of valve causes the same type of traumatic effect upon opening and closing as does the ball and cage valve. Moreover, the blood flow through this type of valve, represented by arrows 104, is diverted by disc 114, resulting in a semicentral flow of the blood with a minimal gradient. As with the ball and cage structure of FIG. 9A, the flow is also directed toward the aortic walls and can cause injury at points 110. Additionally, the flow of blood through valve 112 is marked by turbulence in the aorta near points 110, which can cause trauma to the blood cells. FIG. 9C further illustrates the problems encountered with another type of prior art value 116 employing a tilting disc 118 shown in the open position in the aortic valve position. Because the valve operates in response to pressure differentials, blood cells may be damaged by the impacting surfaces. Moreover, the blood flow, again represented by arrows 104, is diverted by disc 118 toward the aortic walls, causing injury at points 110. The turbulence discussed above with its attendant blood cells damage and hemolysis are additional drawbacks to the effectiveness of this prior art valve. In its broader aspects, the present invention includes any means for using magnetic forces to prevent the impacting of valve surfaces caused by a differential in upstream and downstream pressures. It is thus within the scope of this invention to use the repulsive force induced between magnetic poles having the same polarity to avoid the impact which normally occurs in the type of valves illustrated in FIGS. 9A through 9C when such valves are opened or closed. For example, first and second magnetic elements could be mounted within a disc valve 112 as shown in FIG. 9B such that one pole of a first magnetic element mounted in disc 114 would generate a repulsive force with the same pole of the second magnetic element mounted in the disc surrounding cage of valve 112. By this arrangement, the traumatic impact normally caused upon valve opening by the engagement of disc 114 with the surrounding cage can be entirely avoided.

APPLICATION AND OPERATION OF INVENTION

The following description of the improved valve of the present invention is merely illustrative and is not meant to limit its application, it is contemplated that the novel magnetically-assisted closing device described above could be used in any human or animal structure where a sphincter type action is needed to open or close a structure or organ, especially where there is a naturally-occurring valve. The present invention could also be used as a valve in tubing connecting body cavities or structures, such as in the pleural cavity or peritoneal cavity. In addition, the improved valve could be used outside the body in medical equipment, such as respirators, which utilize valves to control the flow of pulsatory fluids. Another application of the invention concept presented herein lies in the modification of existing prosthetic valves. By way of example, magnetic members exerting a repulsive force could be provided at the tops of the cage struts in a ball and cage type valve. The ball, which would be made of a material responsive to magnetic repulsive force, would be pushed against the cage in the open position by the pressure of the fluid entering the valve and repelled from the cage by the repulsive magnetic force when the fluid pressure dropped, thus magnetically to assume a closed position, in which the ball is seated in the valve seat. This magnetically assisted closing would reduce the amount of turbulence, hence the level of trauma to the blood cells and hemolysis.

The operation of the improved valve of the present invention as it would function if used to replace the aortic valve in a human heart presents a convenient illustration. The improved valve is placed in the aortic position with valve orifice 32 toward the left ventricle and valve outlet 26 of central tube 16 and flaps 18 and 20 extending into the aorta. During systole blood from the left ventricle flows into valve orifice 32 and into central tube 16, exerting sufficient pressure between magnetic members 28 and 30 so that they are forced apart, separating flaps 18 and 20 and permitting central tube 16 to expand to its largest diameter, as shown in FIG. 3. During the end systolic, closing of the valve is initiated by the attractive force exerted between magnetic members 28 and 30. Magnetic members 28 and 30 come together, compressing central tube 16 at 34 to close the valve. During diastole the flexible valve portions 16, 18 and 20 descend in response to the pressure gradient. The valve is then fully closed, as shown in FIG. 4, and ready to respond to other systolic/diastolic cycle.

Other aspects, objects and advantages of this invention can be obtained from a study of the drawings, the disclosure and the appended claims.

I claim:

1. A prosthetic valve for causing unidirectional flow of a pulsatory fluid comprising:
   (a) mounting means positionable upstream within the flow of pulsatory fluid for forming an inlet through which the pulsatory fluid may flow into the valve;
   (b) valve outlet means for moving from a first configuration in which fluid flow through said inlet is cut off to a second configuration in which fluid may freely flow through said inlet from the upstream side to the downstream side of the valve in response to the fluid pressure upstream of the valve increasing above the fluid pressure downstream of the valve, said valve outlet means including a pair of flexible collapsible wall segments positioned on opposite sides of said mounting means, said flexible collapsible wall segments being deformed into contact to close said flow passage when said valve outlet means is in said first configuration, and being moved apart to open said flow passage when said valve outlet means moves to said second configuration; and
   (c) magnetic closure assisting means positioned adjacent the downstream end of said flexible collapsible wall segments providing a continuous bias force to said flexible collapsible wall segments tending to collapse said collapsible material to close said flow passage, said bias force being insufficient to maintain said collapsed condition when the upstream pressure is sufficiently greater than the downstream pressure to move said valve outlet means to said second configuration, said closure assisting means including a pair of opposed magnetic force created elements mounted, respectively, on opposite sides of said flexible collapsible wall segments adjacent the downstream end of said flexible collapsible wall segments.

2. A valve as defined in claim 1, wherein said wall segments are extended laterally and are joined to form a tubular element, said joined wall segments being formed of non-resilient, biologically non-reactive fabric.

3. A valve as defined in claim 2, wherein said closure assisting means includes a pair of permanent magnets positioned on laterally opposite sides adjacent the downstream end of said flexible collapsible wall segments.

4. A valve as defined in claim 3, wherein said closure assisting means includes a pair of flexible non-resilient flaps connected at one end to said valve support means and at the other end to said pair of permanent magnets, respectively.

5. A valve as defined in claim 4, wherein said tubular element includes an internal dividing web joining the opposed inside wall surfaces of said tubular element, said internal dividing web being positioned to form a bifurcated passage for fluid flow through said tubular element when said valve outlet means is moved to said second configuration.

6. A valve as defined in claim 2, wherein said tubular element includes a pair of rigid projections positioned on opposite sides of said mounting means and extending downstream between said flexible collapsible wall segments, said pair of rigid projections forming a sealing engagement with said wall segments when said valve outlet means is in said first configuration, said closure assistance means including a pair of permanent magnets attached to the downstream ends of said wall segments, respectively, and being arranged to provide a mutually attractive force tending to pull said wall segments together.

7. A valve as defined in claim 4, wherein said valve outlet means includes a pair of rigid projections connected to opposed sides of said mounting means and extending in a downstream direction, said rigid projections providing support to said collapsible wall segments when said valve outlet means is in said first configuration.

8. A valve as defined in claim 7, wherein each said rigid projection includes two substantially arcuate protrusions on the downstream side.

9. A valve as defined in claim 1, wherein said mounting means includes a semi-rigid ring and a fabric material covering at least the outside surface of said ring to provide a suture holding surface for retaining said valve when implanted.

10. A valve, as defined in claim 1, wherein said flexible collapsible wall segments form a generally tubular element.

* * * * *